US00PP25032P3

(12) United States Plant Patent
Suphachadiwong

(10) Patent No.: US PP25,032 P3
(45) Date of Patent: Nov. 4, 2014

(54) ***PHALAENOPSIS* PLANT NAMED 'SUPHAL1308'**

(50) Latin Name: ***Phalaenopsis* hybrid**
Varietal Denomination: SUPHAL1308

(71) Applicant: Thumrong Suphachadiwong, Chonburi (TH)

(72) Inventor: Thumrong Suphachadiwong, Chonburi (TH)

(73) Assignee: Suphachatawong Innovation (TH)

( * ) Notice: Subject to any disclaimer, the term of this patent is extended or adjusted under 35 U.S.C. 154(b) by 39 days.

(21) Appl. No.: 13/815,796

(22) Filed: Mar. 15, 2013

(65) Prior Publication Data

US 2014/0283259 P1 Sep. 18, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell

(74) *Attorney, Agent, or Firm* — Cassandra Bright

(57) ABSTRACT

A new and distinct *Phalaenopsis* cultivar named 'SUPHAL1308' is disclosed, characterized by compact plant size, purple flowers with white edges and red-purple lip. The new variety is a *Phalaenopsis*, typically produced as an indoor ornamental plant.

2 Drawing Sheets

Figure 1:
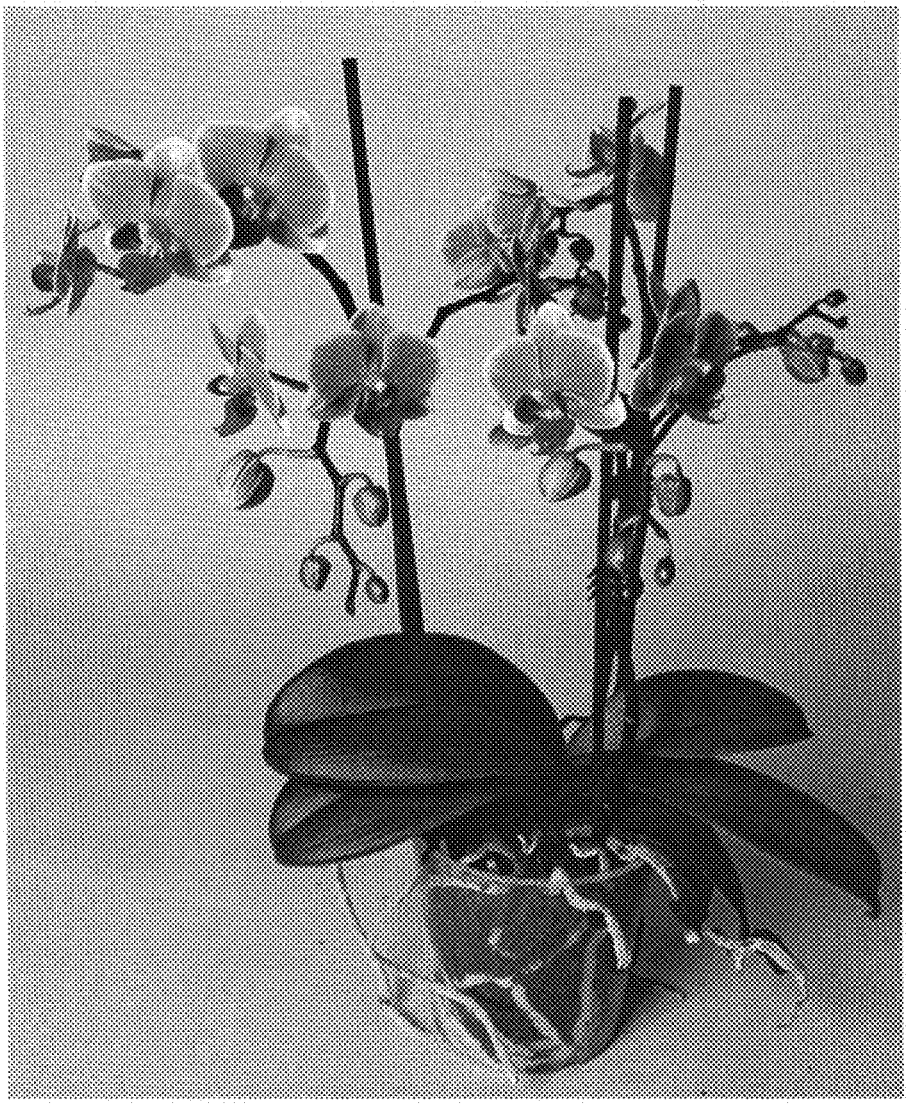

Latin name of the genus and species: *Phalaenopsis* hybrid. Variety denomination: 'SUPHAL1308'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'BTXS6' with the unpatented, proprietary pollen parent referred to as *Phalaenopsis* 'RR5S2'. The crossing was made by the inventor in his research greenhouse in Chonburi, Thailand in September of 2005.

The new variety was first selected by the inventor, Thumrong Suphachadiwong, a citizen of Thailand, in November of 2008 in a research greenhouse belonging to the inventor in Chonburi, Thailand. After identifying the new variety as a potentially interesting selection, the inventor continued confidential testing and propagation of 'SUPHAL1308', assessing stability of the unique characteristics of this variety.

Asexual reproduction of the new cultivar 'SUPHAL1308' was first performed at a commercial laboratory belonging to the inventor in Chonburi, Thailand by tissue culture in December of 2008. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1308' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1308'. These characteristics in combination distinguish 'SUPHAL1308' as a new and distinct *Phalaenopsis* cultivar:

1. Compact plant size.
2. Purple flowers with white edges.
3. Red-purple lip.
4. Fine speckling on interior of labellum

PARENT COMPARISON

Plants of the new cultivar 'SUPHAL1308' are similar to the seed parent, *Phalaenopsis* 'BTXS6' in most horticultural characteristics. The new variety, however, produces larger and darker colored flowers than the seed parent.

Plants of the new cultivar 'SUPHAL1308' are similar to the pollen parent, *Phalaenopsis* 'RR5S2' in most horticultural characteristics. Plants of the new variety however produce a different flower color as well as a more compact plant than the pollen parent.

COMMERCIAL COMPARISON

'SUPHAL1308' is similar to the unpatented commercial variety *Phalaenopsis* 'F2269' in most horticultural characteristics. However the new variety, 'SUPHAL1308' differs from 'F2269' in the following characteristics:

1. Sepals and petals have wider margin of white.
2. Larger flower size.
3. Narrower and darker green leaves.
4. Different apical lobe shape.

5. Different dorsal sepal shape.
6. Callus is lighter yellow.

BRIEF DESCRIPTION OF THE PHOTOGRAPH

The accompanying photographs in FIG. 1 illustrates in full color a typical plant of 'SUPHAL1308' grown in a commercial greenhouse in Zuidbroek, the Netherlands. This plant is approximately 18 months old after deflasking, shown planted in an 11 cm container.

Figure 2:
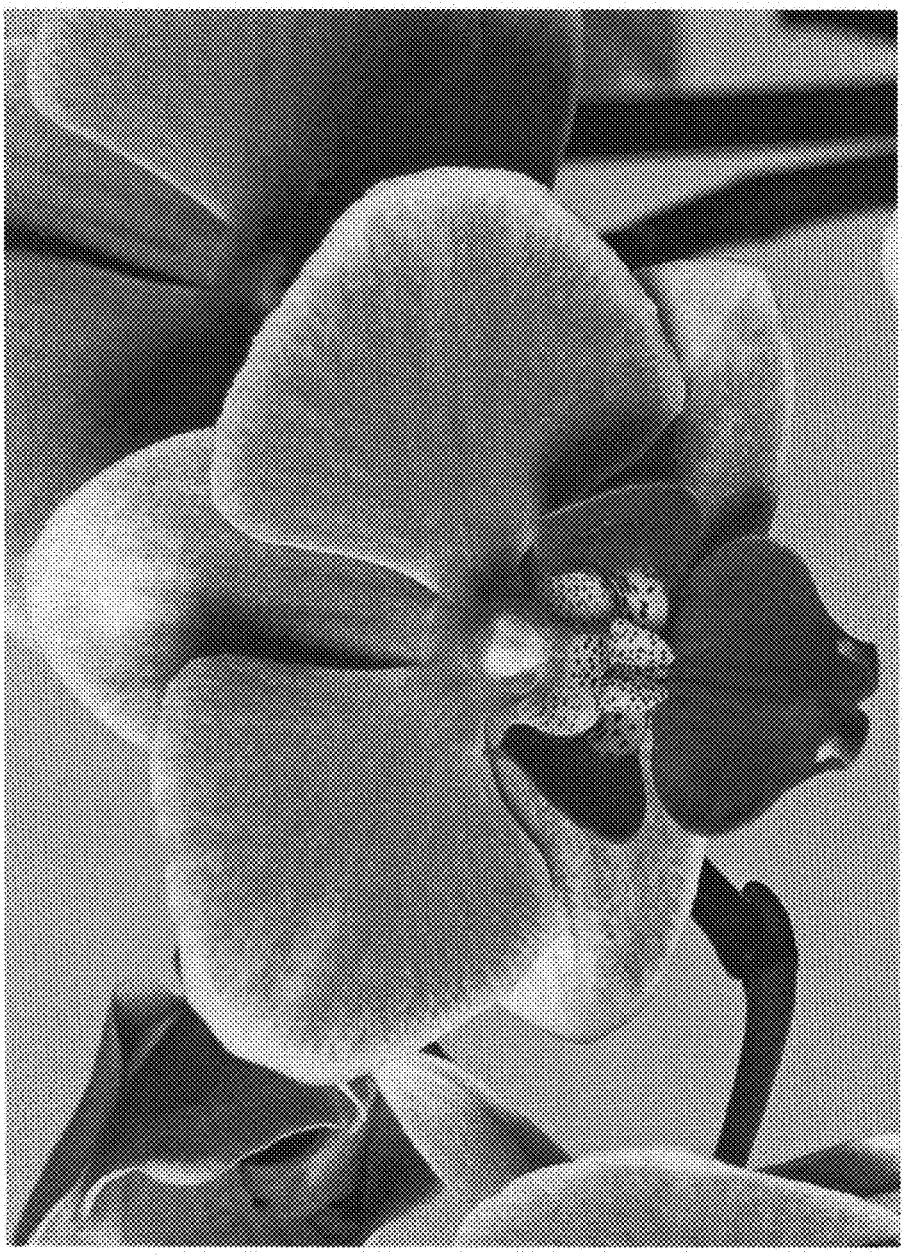

FIG. 2 illustrates a close up of the individual flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SUPHAL1308' plants grown in a commercial greenhouse in Zuidbroek, the Netherlands. This plant is approximately 18 months old after deflasking, shown planted in an 11 cm container. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1308'.

PROPAGATION

Type of propagation typically used: Tissue culture.

Time to initiate roots: About 21 days at approximately 28° C.

Time to produce a rooted cutting/liner: About 26 weeks at approximately 18° C. to 28° C.

Root description: Thick (typical for *Phalaenopsis*) and rounded, average diameter: 5 mm, colored greyed-green; near RHS 194A to 194B.

PLANT

Growth habit: Monopodial.

Height from top of soil line to top of foliage: Average 9.6 cm.

Height from top of soil line to top of flowers: Average 31.0 cm.

Plant spread: At widest, average: 35.2 cm; at narrowest: 27.9 cm.

Normal pot size: 11 cm.

Growth rate: Moderate.

Number of leaves per plant: Average 8.

FOLIAGE

Leaf:

- *Arrangement*.—Distichous.
- *Average length*.—Approximately 14.9 cm (including sheath).
- *Average width*.—Approximately 6.3 cm.
- *Shape of blade*.—Elliptic.
- *Aspect*.—Horizontal to slightly upward, slightly curled downward.
- *Apex*.—Unequal acute, pointed downward.
- *Base*.—Cuneate. Sheath length: Average 1.5 cm. Sheath width: Average 1.3 cm. Sheath color: Green; near RHS 143A.
- *Margin*.—Entire.
- *Texture of top surface*.—Smooth, slightly furrowed.
- *Texture of bottom surface*.—Smooth.
- *Appearance*.—Moderately glossy on all surfaces.
- *Color*.—Young foliage upper side: Green; near RHS N137A. Young foliage under side: Yellow-green; near RHS 146A. Mature foliage upper side: Green; near RHS N137A. Mature foliage under side: Yellow-green; near RHS 146A.
- *Venation*.—Type: Camptodromous. Venation coloration. Upper side green; slightly darker than near RHS 137A, main vein green; near RHS 147A, under side yellow-green; near RHS 146A, main vein on under side green; near RHS 143A.

Petiole: No petioles present.

FLOWERING CHARACTERISTICS

Flower bud:

- *Rate of opening*.—Fully opened approximately five days after stage described.
- *Length*.—Approximately 1.4 cm.
- *Diameter*.—Approximately 1.2 cm wide and 1.4 cm high.
- *Shape*.—Broad ovate.
- *Color*.—Greyed-orange; near RHS 177D, base tinged yellow-green; near RHS 150B.

Peduncle:

- *Length*.—Approximately 32.8 cm.
- *Width*.—Approximately 0.5 cm.
- *Aspect*.—Approximately 60° angle to rosette.
- *Strength*.—Strong.
- *Texture*.—Smooth.
- *Appearance*.—Very slightly glossy.

Inflorescence:

- *Flowers per stem*.—Average 18.
- *Inflorescence arrangement*.—Compound panicle.
- *Inflorescence height*.—Approximately 12.0 cm (measured from lowest branching of panicle to top of inflorescence).
- *Inflorescence width*.—Approximately 17.8 cm.

Individual flowers:

- *Flower type*.—Single zygomorphic flower.
- *Shape*.—Rounded deltate.
- *Length (height)*.—Approximately 5.0 cm.
- *Width*.—Approximately 5.3 cm.
- *Depth*.—Approximately 2.5 cm.
- *Fragrance*.—No fragrance.
- *Persistent*.—Non-persistent.
- *Quantity of petals*.—2 true petals.

Petals:

- *Arrangement*.—One petal on each side of the column.
- *Length*.—Approximately 2.5 cm.
- *Width*.—Approximately 2.8 cm.
- *Shape*.—Deltoid.
- *Apex*.—Obtuse.
- *Base*.—Cuneate.
- *Margin*.—Entire.
- *Texture*.—Upper (forward) surface: Smooth, velvety.
- *Texture*.—Lower (back) surface: Smooth, velvety.
- *Appearance*.—Matte on both surfaces.

*Color*.—When opening, forward surface: Purple; near RHS N78B, margins white; near RHS N155A to NN155D. When opening, back surface: Purple; near RHS N78C and N78D at the base, margins white; near RHS N155A. Fully Opened, forward surface: Purple; near RHS N78B, margins white; near RHS N155A. Fully Opened, back surface: Purple; near RHS N78C and N78D at the base, margins white; near RHS N155A. Fading, forward surface: Not fading, only becoming non-velvety. Fading, back surface: Not fading, only becoming non-velvety.

*Color venation*.—Fully Opened, forward surface: Only main vein slightly visible, colored purple; near RHS N78A. Fully Opened, back surface: Only main vein slightly visible, colored purple; near RHS N78B.

Labellum:

*Shape*.—Three-parted.

*Length*.—Approximately 2.3 cm.

*Width*.—Approximately 1.4 cm.

*Texture*.—Smooth, velvety.

*Appearance*.—Matte.

*Tip*.—Cleft, tips cirrhose.

*Base*.—Cuneate.

*Color*.—When opening, forward surface: Central lobe purple; near RHS N79C, tinged red-purple towards the base; 71A, lateral lobes red-purple; near RHS 71A, base white; near RHS NN155C, moderately dotted red-purple; near RHS 71A, callosities yellow; near RHS 9C, dotted red-purple; near RHS 71A. When opening, back surface: Central lobe red-purple; near RHS 72B, with a lighter, broad central band; near RHS 76C, lateral lobes red-purple; near RHS 72A, base white; near RHS NN155C. Fully Opened, forward surface: Central lobe purple; near RHS N79C, tinged red-purple towards the base; 71A, lateral lobes red-purple; near RHS 71A, base white; near RHS NN155C, moderately dotted red-purple; near RHS 71A, callosities yellow; near RHS 9C, dotted red-purple; near RHS 71A. Fully Opened, back surface: Central lobe red-purple; near RHS 72B, with a lighter, broad central band; near RHS 76C, lateral lobes red-purple; near RHS 72A, base white; near RHS NN155C. Fading, forward surface: Not fading, only becoming non-velvety. Fading, back surface: Not fading, only becoming non-velvety.

*Color venation*.—Fully Opened, forward surface: No venation visible. Fully Opened, back surface: No venation visible. Margin: Entire.

Sepals:

*Quantity*.—3.

*Length*.—Dorsal sepal approximately 2.6 cm. Lateral sepals approximately 2.5 cm.

*Width*.—Dorsal sepal approximately 2.1 cm. Lateral sepals approximately 2.0 cm.

*Shape*.—Ovate.

*Apex*.—Obtuse.

*Base*.—Broad cuneate.

*Margin*.—Entire.

*Texture*.—Smooth, velvety.

*Appearance*.—Matte.

*Color*.—Fully Opened, forward surface: Purple; near RHS N78B, veined darker; near RHS N78A, top and margins white; near RHS NN155C, lateral sepals with a conspicuous white to greyed-yellow spot at the base; near RHS 155A to 160D, spot finely dotted purple; near RHS N78A. Fully Opened, back surface: Purple; near RHS 77D, top and margins white; near RHS NN155C.

Pedicels:

*Length*.—Approximately 2.5 cm.

*Diameter*.—Approximately 0.25 cm.

*Angle*.—Approximately 85° to peduncle.

*Strength*.—Moderately strong.

*Texture*.—Smooth.

*Appearance*.—Moderately glossy.

*Color*.—Yellow-green; near RHS 148D, darker towards the base; near RHS 148B.

REPRODUCTIVE ORGANS

*Stamens, style and stigma fused into column*?.—Yes.

*Column length*.—Approximately 0.8 cm.

*Column diameter*.—Approximately 0.5 cm.

*Column color*.—Purple; near RHS 78B.

*Ovary*.—Position: Inferior. Diameter: Approximately 0.3 cm. Color: Purple; near RHS 76B.

*Pollen color*.—Yellow-orange; near RHS 23A.

OTHER CHARACTERISTICS

Disease resistance: Neither resistance nor susceptibility to the normal diseases found in *Phalaenopsis* has been observed.

Drought tolerance and cold tolerance: Normal for species.

Fruit/seed production: No fruits/seeds detected to date.

What is claimed is:

1. A new and distinct cultivar of *Phalaenopsis* plant named 'SUPHAL1308' as herein illustrated and described.

* * * * *